United States Patent [19]

Widman et al.

[11]  4,370,136

[45]  Jan. 25, 1983

[54] TREATMENT FOR PERIODONTAL DISEASES

[76] Inventors: Lawrence E. Widman, 315 W. Glenside Ave., Glenside, Pa. 19038; Nasser G. Habeeb, 257 Albany Ave., Kingston, N.Y. 12401; Raymond Z. Darakjian, 531 Summit St., Englewood Cliffs, N.J. 07632

[21] Appl. No.: 259,583

[22] Filed: May 1, 1981

Related U.S. Application Data

[63] Continuation-in-part of Ser. No. 882,941, Mar. 2, 1978, abandoned.

[51] Int. Cl.³ .............................................. A61K 6/08
[52] U.S. Cl. ...................................... 433/217; 106/35
[58] Field of Search ............... 433/201, 217, 228, 202; 106/35; 260/998.11

[56] References Cited

U.S. PATENT DOCUMENTS

| | | | |
|---|---|---|---|
| Re. 27,682 | 6/1973 | Schnell et al. | 260/37 PC |
| 3,408,225 | 10/1968 | Streib et al. | 117/126 |
| 3,541,049 | 11/1970 | Cleveland | 260/37 PC |
| 3,559,288 | 2/1971 | Rehberg et al. | 32/2 |
| 3,678,079 | 7/1972 | Carty et al. | 260/37 PC |
| 3,971,134 | 7/1976 | Bokros | 32/10 A |
| 4,060,896 | 12/1977 | Wahnish | 32/10 A |
| 4,164,794 | 8/1979 | Spector et al. | 32/10 A |

*Primary Examiner*—Lorenzo B. Hayes
*Attorney, Agent, or Firm*—Cooper, Dunham, Clark, Griffin & Moran

[57] ABSTRACT

Bone resorption from and invagination of epithelial tissue around periodontally involved teeth can be arrested and reversed by coating the affected areas of the tooth roots with a nontoxic, biocompatible composition which acts as a shield against bacterial toxins and which is capable of supporting biological attachment of cells in the gingiva. This treatment allows the periodontally involved region to heal by providing improved physiological and mechanical support of the tooth by its bone socket. In a preferred embodiment of the invention, the treatment involves coating the root surfaces of periodontally involved teeth with a film consisting of a polycarbonate resin in methylene chloride solvent.

This invention also provides a process for stopping and reversing resorption of bone from, and invagination of epithelial tissue around, screws, pins, blades, and other metal inserts which have been placed in bones, particularly dental implants placed in alveolar bone. The process involves coating the osseous or subgingival segment of the insert with a nontoxic, bioacceptable composition which is capable of supporting biological attachment of fibroblastic or epithelial cells. The preferred coating is a polycarbonate resin.

5 Claims, No Drawings

TREATMENT FOR PERIODONTAL DISEASES

This application is a continuation-in-part of U.S. application Ser. No. 882,941, now abandoned, filed Mar. 2, 1978, the disclosure of which is hereby incorporated by reference into the present disclosure. A disclosure document for this invention, Ser. No. 047,785, was filed on Mar. 15, 1976 U.S. Pat. No. 4,273,063 June 16, 1981. It is also hereby incorporated by reference into this application.

BACKGROUND OF THE INVENTION

Inflammatory periodontal disease (periodontitis) is a widely prevalent oral disease. In its severe form, it is characterized by gradual resorption of the alveolar bone which retains and supports the teeth. The affected teeth become loose, and eventually are supported inadequately for retention in the mouth. Commonly, more than one tooth is affected simultaneously and it is not unusual for ten or twenty teeth to be lost during the same period.

Present therapy for periodontal disease involves surgical removal of healthy bone in an attempt to eliminate gingival pocket depth which retains all bacteria and thereby to slow progression of the disease. Chemical therapies, such as use of weak acids to wash the involved root surfaces, have not provided satisfactory results in severe forms of the disease. Previously, no one has suggested use of a polymer to treat periodontal disease.

The primary cause of periodontal disease is thought to be the presence of bacterial toxins in the diseased root which cause failure of gingival cells to maintain a topologically continuous, bacteria-tight seal around the tooth root. It is theorized that bacteria colonize exposed root surfaces, where they or their toxic products, or both, cause further detachment of gingiva and, in severe cases, resorption of proximal alevolar bone. Regular mechanical debridement leads to some improvement, supporting current thinking about the primary cause of the disease. However, attempts to maintain a bacteria-free environment have not been generally effective in cases within which bone loss has occurred and an open soft tissue cuff or pocket exists.

The present invention solves this problem by interposing between the diseased tooth root surface and the overlying gingiva a material which permits mammalian cells to attach biologically. By using a material which is also impermeable to the toxic products of bacteria which have colonized the root surface, biological reattachment of the gingiva and reapproximation of alveolar bone are encouraged.

Although some plastics support attachment and growth of mammalian fibroblastic and epithelial cells (which are the major living constituents of normal gingiva) in cell culture, certain of these, such as polystyrene, require toxic or cumbersome pre-treatments to enable the to do so, including acid washes or electron bombardment inside a glow discharge apparatus. Other plastics, such as methylmethacrylate, do not permit biological attachment of mammalian cells in vivo or in vitro. Still others, such as teflon, may permit biological attachment of mammalian cells in both animal and in culture, but are not useful as coatings because they are insoluble and cannot be cast as a film.

In the event of extensive tooth loss due to inflammatory periodontal disease or trauma, it is not possible to provide patients with fixed dentures because insufficient structural support remains in the mouth. Current therapy involving insertion of dental implants to which fixed dentures may be attached is unsatisfactory. The implants are unreliable and have high failure frequencies because of lack of gingival attachment to the implants and bacterial migration along the implants which lead to resorption of the alveolar bone which supports and retains them. The reasons for bone resorption around implants and around periodontally involved tooth roots are believed to be identical, namely, bacteria penetrate between the implant and the gingival soft tissue and secrete toxins promoting epithelial invagination and bone resorption. The process may be more severe in implants. Periodontally involved tooth roots usually have some degree of gingival attachment at the base of epithelial invagination to protect them from bacterial invasion, but, currently available implants are unable to form a bacteria-tight seal with the gingival tissue. Although the gingival tissue presses closely againt the implant, there is access for bacteria to enter and multiply. One reason these implants do not form protective seals is that their outer surfaces are made of materials unable to support biological attachment of mammalian cells.

Although a wide variety of materials are used, most implants involve porous outer layers to encourage fibrous ingrowth for mechanical support. Examples of such porous coatings are vitreous carbon (U.S. Pat. No. 3,971,134; 1976) and mixtures of polymethacrylate with grated anorganic bone (U.S. Pat. No. 3,609,867; 1971). U.S. Pat. No. 3,971,134 also discloses biologically inert polymers such as polymethylmethacrylate, polyethylene, and polytetrafluoroethylene as porous implant coatings. Finally, U.S. Pat. No. 3,906,550 (1975) discloses fiber metal implant coatings.

Other coatings include calcium compounds (U.S. Pat. No. 3,984,914; 1976) to promote formation of cemetoid-type structures around the implant and nonporous polymethylmethacrylate (U.S. Pat. No. 4,060,896; 1977). However, neither coating forms a bacteria-tight seal with alveolar bone. Methacrylate, in particular, is incapable of molecular attachment to tissue (Hammer, J. E. and O. M. Reed., J. Biomed. Mater. Res. Symposium 1972, 2 (pt 2), 297–310). Instead, the body forms fibrous capsules around the methacrylate. In general, the prior art teaches that nonporous implant coatings, e.g. methacrylate, would be less effective than porous coatings of the same composition because of inadequate mechanical support associated with nonporous coatings. In this way, the art teaches away from the present invention by disclosing the use of porous, biologically inert materials, such as methylmethacrylate, carbon, and the like.

The materials presently used as coatings in prosthetic devices, such as orthopedic and maxillofacial prostheses, also teach away from this invention. Typically, the coatings are porous and have the deficiencies described above. These materials also exhibit high creep or poor load distribution under stress, or both (U.S. Pat. No. 4,164,794; 1979). Non-porous bioglasses have been used in prosthetic devices to promote direct bone-to-implant bonding (Griss, P. et al., J. Biomed. Mater. Res. 1976, 10, 511–518 and Blencke, B. A. et al., J.Biomed.-Mater.Res. 1978, 12, 307–316). However, bioglasses do not form bonds with soft tissues (Clark, et al., J.Biomed.Mater.Res. 1976, 10, 161–174). None of these disclosures teach the use of nonporous, polymeric coatings in applications involving soft tissue (e.g., gingiva.) All involve hard tissue (e.g., fractured bone.)

SUMMARY OF THE INVENTION

This invention provides a method for treating periodontal disease and for preventing rejection of dental implants by coating affected tooth roots or implants, respectively, with a nontoxic, biocompatible organic polymer capable of supporting biological attachment of mammalian cells and impermeable to bacterial toxins which may permeate the diseased tooth root, inhibiting any form of gingival reattachment.

The progress of bone resorption from around periodontally involved tooth roots may be arrested or reversed by presenting to the surrounding tissue a surface which is acceptable to the tissue as a substrate for cell attachment and which protects the tissue from bacterial toxins. The process involves coating the affected area of the tooth root with a nontoxic, impermeable, biocompatible organic polymer which readily allows gingival cells to attach to it and which promotes biological integrity between the surrounding soft tissue and the root.

The invention also provides a process for arresting and reversing the progress of bone resorption from around dental implants by presenting to the surrounding tissue a surface which is acceptable as a substrate for cell attachment and which promotes formation of a bacteria-tight seal. The process involves forming a polymeric shield around the implant to separate it from surrounding tissue, allow fibroblast and epithelial cells to attach to its surface, and promote biological integrity between soft tissue and implant.

Finally, this invention concerns coated dental implants which are capable of supporting biological attachment of gingival cells and are impermeable to bacterial toxins.

polycarbonate refers to any of the various types of resins generally known as or described by this term including those prepared by vinyl polymerization of unsaturated carbonate esters; those formed by the reaction of dihydroxy-monoaryl compounds such as hydroquinone and resorcinol with phosgene, carbonate esters or other carbonate precursors; and those prepared by the reaction of bisphenols with polycarbonate-forming derivatives of carbonic acid. Polycarbonates useful in the practice of this invention are described in U.S. Pat. Nos. 3,559,288 (1971); 3,678,079 (1972); 3,408,225 (1968); and Re27,682 (1973). The disclosures of these patents are hereby incorporated by reference into the present disclosure.

One polycarbonate which has been found useful in the practices of this invention is marketed under the trademark LEXAN by the General Electric Company, Sheet Products Section, Plastics Business Division, 1 Plastics Avenue, Pittsfield, Massachusetts 01201. This product is described in General Electric Technical Report CDC-396 (Revision H) dated May 1, 1978. In particular, natural LEXAN film (Grade 8070-112) has been found useful. LEXAN's properties are summarized in Table I.

TABLE I

SUMMARY OF PROPERTIES OF LEXAN

| PROPERTY OR CHARACTERISTIC | TEST | UNITS | VALUE |
| --- | --- | --- | --- |
| 1. Area Factor | | $in^2$ per lb. | 23,100 (one-mil film) |
| 2. Specific Gravity | | | 1.20 |
| 3. Tensile Yield Strength | ASTM D-882-56T | psi | 8,400–8,800 |
| 4. Elongation | ASTM D-882-56T | % | 85–105 |
| 5. Bursting Strength | ASTM D-774 | Mullen Points | 25–35 (on 4-mil film) |
| 6. Tearing Strength | Elmendorf | g/mil | 20–25 |
| 7. Tearing Strength | ASTM D-1004 | lbs/in | 1150–1570 |
| 8. Folding Endurance | ASTM D-643-43 (B) | | 250–400 |
| 9. Water Absorption (24 Hr.) | ASTM D-570 | % | 0.35 |
| 10. Dielectric Constant at 25° C. | 60 cycles | | 2.99 |
| | 1 KC | | 2.99 |
| | 1 MC | | 2.93 |
| 11. Power Factor at 25° C. | 60 cycles | % | 0.10–0.23 |
| | 1 KC | | 0.13 |
| | 1 MC | | 1.10 |
| 12. Dielectric Strength | S/S in air | volts/mil | 1,500 |
| 13. Volume Resistivity at 25° C. | | ohm/cm | $10^{16}$ |

DETAILED DESCRIPTION OF THE INVENTION

Periodontally involved teeth may be treated and the rejection of dental implants prevented if the surface of the periodontally involved tooth roots or the implant, respectively, are coated with a polymeric material which is nontoxic, biocompatible, capable of supporting biological attachment of gingival cells and impermeable to bacterial toxins present within the diseased root.

Although any polymer which satisfies these criteria is useful in the practice of this invention, the presently preferred polymer is polycarbonate. As used herein, Polycarbonate, in particular, also has the advantages of being soluble in nontoxic organic solvents, from which it can be cast as a film; of attaching firmly as a cast film to wet, freshly extracted tooth roots; of being very strong mechanically; of being available in a range of colors so as to make it useful in forming the main structural element in artificial implants; and of being moldable and machinable so as to make it useful in the formation of ancillary dental implant structures such as outer sheaths and screws.

Although, as indicated, a wide range of polycarbonate resins are useful, those having a relative viscosity from about 1.20 to 1.40, particularly from about 1.25 to about 1.32, measured in a 0.5 percent solution of methylene chloride at 20° C. have been found most useful. In addition to the polycarbonate, various materials such as fillers, antioxidants, plasticers, dyes, stabilizers, and the like may be employed with the polymer.

For treating periodontally-involved tooth roots the invention involves the application of a nontoxic, biocompatible polymer onto the dried surface of the affected area of the tooth root and additionally onto an appropriate margin of normal root. By so applying the coating, it is possible to form a shield against bacterial toxins and thereby provide an environment which is capable of supporting biological attachment of cells in the gingiva.

Prior to applying the coating the root is prepared by exposing it using standard dental techniques such as reflection of a gingival flap with a surgical margin. This is followed by degranulation of the area, root planning, and maintenance of a dry field by standard isolation methods. The coating is preferably cast directly onto the root surface from a solution of a suitable polymer such a polycarbonate in a suitable solvent such as methylene chloride. This results in the formation of a thin, yet unbroken film covering the surface. After this film dries, the wound is closed.

In modifications of the invention, the dry root surface may be etched using standard dental techniques to create pits which will promote adherence of the plastic film. Also, the dried and etched, if desired, root surface may first be coated with a polymer such as a dental adhesive, e.g., cyanoacrylate, which is allowed to dry prior to application of the plastic film and permits greater adherence by providing intermediate bonding of superior strength to that obtained with the polymer alone. Finally, complete drying of the cast film may be promoted by exposure of the film to a stream of hot air as, for example, from a hair dryer or like instrument.

This invention also provides a method for stopping and reversing bone resorption from, and invagination of epithelial tissue around, screws, pins, blades, and other dental implants which are placed in alveolar bone. This process involves coating the osseous or subgingival segment of the insert or implant with a nontoxic, biocompatible polymeric composition which is capable of supporting biological attachment of fibroblastic or epithelial cells. The preferred polymer for this purpose is again polycarbonate.

The practice of this invention will be better understood by reference to the example which follows although it is to be understood that this example is not intended to limit in any way the scope of the invention as set forth in the claims.

EXAMPLE 1

The beagle dog was chosen as an experimental model because it is the standard model for human periodontal disease used in modern dental research.

An old beagle dog (estimated age of 8 to 10 years) was obtained from a reliable, established biomedical animal supply house and was treated as follows:

Following preoperative medication with acepromazine maleate and atropine sulfate, general anesthesia was induced with thiamyl sodium (5%) and maintained with nitrous oxide and metofane. Local anesthesia was established by mucobuccal fold and papillary infiltration with 2% xylocaine and epinephrine (1:100,000 weight/weight).

Full-thickness flaps were reflected in areas of pre-existing periodontal disease. The roots were curretted thoroughly. A solution of 10% (weight/volume) polycarbonate[1] in methylene chloride was painted on the areas of study and dried mechanically. The flaps were repositioned to their original sites with sutures. Control sites were treated similarly except for painting with polycarbonate solution. Prophylactic antibiotics and soft diet were prescribed. Periodontal status was reevaluated at three weeks.

[1] LEXAN film, Grade 8070-112

The treated and control areas were evaluated on a clinical level by the use of a periodontal probe to test periodontal pocket depth. Some areas that had been treated with polycarbonate film displayed marked reduction in probe depth (seven millimeters reduced to three millimeters (normal range: zero to three millimeters). In contrast, control areas and areas were the film of polycarbonate was exfoliated showed no change in probe depth. Other techniques, such as applying the shield as a preformed film, e.g., a packing which is forced along the root surface without incising the gingiva, or as a rigid insert, may be alternative methods of practicing this invention.

What is claimed is:

1. A method for treating the resorption of bone from around the root surfaces of periodontally involved natural teeth which comprises coating said surfaces with a nontoxic, biocompatible composition containing a polycarbonate resin dissolved in a nontoxic organic solvent and which is capable of supporting biological attachment of gingival cells and is impermeable to bacterial toxins.

2. A method in accordance with claim 1 wherein said polycarbonate resin has a relative viscosity from about 1.20 to 1.40 in 0.5 percent methylene chloride at 20° C.

3. A method in accordance with claim 1 wherein said polycarbonate resin is applied to said surface as a film containing polycarbonate and solvent in which the concentration of polycarbonate is in the range 0.5 percent to 95 percent by weight.

4. A method in accordance with claim 3 wherein said solvent is methylene chloride.

5. A coated tooth root prepared in accordance with the method of claim 1.

* * * * *